(12) United States Patent
Rosser

(10) Patent No.: US 11,553,734 B2
(45) Date of Patent: Jan. 17, 2023

(54) CARTRIDGES FOR VAPORIZER DEVICES

(71) Applicant: JUUL Labs, Inc., San Francisco, CA (US)

(72) Inventor: Christopher James Rosser, Cambridge (GB)

(73) Assignee: JUUL Labs, Inc., San Francisco, CA (US)

(\*) Notice: Subject to any disclaimer, the term of this patent is extended or adjusted under 35 U.S.C. 154(b) by 506 days.

(21) Appl. No.: 16/677,121

(22) Filed: Nov. 7, 2019

(65) Prior Publication Data

US 2020/0146360 A1 May 14, 2020

Related U.S. Application Data

(60) Provisional application No. 62/757,262, filed on Nov. 8, 2018.

(51) Int. Cl.
| | |
|---|---|
| *A24F 13/00* | (2006.01) |
| *A24F 17/00* | (2006.01) |
| *A24F 25/00* | (2006.01) |
| *A24F 40/42* | (2020.01) |
| *A61M 11/04* | (2006.01) |
| *A24B 15/167* | (2020.01) |

(52) U.S. Cl.
CPC ............ *A24F 40/42* (2020.01); *A24B 15/167* (2016.11); *A61M 11/042* (2014.02)

(58) Field of Classification Search
CPC .......... A24F 40/10; A24F 40/42; A24F 40/44; A24F 40/48; A24B 15/167; A61M 11/042
See application file for complete search history.

(56) References Cited

U.S. PATENT DOCUMENTS

| | | | |
|---|---|---|---|
| 4,648,393 | A | 3/1987 | Landis et al. |
| 4,708,151 | A | 11/1987 | Shelar |
| 4,793,365 | A | 12/1988 | Sensabaugh et al. |
| 4,819,665 | A | 4/1989 | Roberts et al. |

(Continued)

FOREIGN PATENT DOCUMENTS

| | | |
|---|---|---|
| CA | 2729601 C | 9/2013 |
| CN | 102612361 A | 7/2012 |

(Continued)

*Primary Examiner* — Abdullah A Riyami
*Assistant Examiner* — Thang H Nguyen
(74) *Attorney, Agent, or Firm* — Mintz Levin Cohn Ferris Glovsky and Popeo, P.C.

(57) ABSTRACT

Cartridges for vaporizer devices are provided. In one exemplary embodiment, the cartridge can include a reservoir configured to contain a plurality of encapsulated particles and an airflow tube extending through the reservoir. Each of the plurality of encapsulated particles includes a core formed of a liquid vaporizable material and a coating material that forms a shell surrounding the core, in which the shells of the plurality of encapsulated particles are configured to be selectively ruptured to release the liquid vaporizable material therefrom. The airflow tube includes a wicking element that is in communication with the reservoir, in which the wicking element is configured to draw, into the airflow tube for vaporization, at least a portion of the liquid vaporizable material that is released by rupturing one or more shells of the plurality of encapsulated particles. Vaporizer devices are also provided.

20 Claims, 3 Drawing Sheets

(56) References Cited

U.S. PATENT DOCUMENTS

| | | |
|---|---|---|
| 4,924,883 A | 5/1990 | Perfetti et al. |
| 4,938,236 A | 7/1990 | Banerjee et al. |
| 4,941,483 A | 7/1990 | Ridings et al. |
| 5,019,122 A | 5/1991 | Clearman et al. |
| 5,042,509 A | 8/1991 | Banerjee et al. |
| 5,224,498 A | 7/1993 | Deevi et al. |
| 5,388,574 A | 2/1995 | Ingebrethsen et al. |
| 5,845,649 A | 12/1998 | Saito et al. |
| 5,865,186 A | 2/1999 | Volsey et al. |
| 6,062,213 A | 5/2000 | Fuisz et al. |
| 6,095,153 A | 8/2000 | Kessler et al. |
| 6,164,287 A | 12/2000 | White |
| 6,196,218 B1 | 3/2001 | Voges |
| 6,344,222 B1 | 2/2002 | Cherukuri et al. |
| 6,708,846 B1 | 3/2004 | Fuchs et al. |
| 7,243,689 B2 | 7/2007 | Py |
| 7,290,549 B2 | 11/2007 | Banerjee et al. |
| 7,434,584 B2 | 10/2008 | Steinberg |
| 7,581,540 B2 | 9/2009 | Hale et al. |
| 7,832,397 B2 | 11/2010 | Lipowicz |
| 7,913,686 B2 | 3/2011 | Hughes et al. |
| 8,091,558 B2 | 1/2012 | Martzel |
| 8,251,060 B2 | 8/2012 | White et al. |
| 8,387,612 B2 | 3/2013 | Damani et al. |
| 8,402,976 B2 | 3/2013 | Fernando et al. |
| 8,485,180 B2 | 7/2013 | Smutney et al. |
| 8,714,161 B2 | 5/2014 | Liu et al. |
| 8,733,345 B2 | 5/2014 | Siller |
| 8,807,131 B1 | 8/2014 | Tunnell et al. |
| 8,813,759 B1 | 8/2014 | Horian |
| 8,833,364 B2 | 9/2014 | Buchberger |
| 8,851,083 B2 | 10/2014 | Oglesby et al. |
| 8,991,402 B2 | 3/2015 | Bowen et al. |
| 9,016,274 B1 | 4/2015 | White |
| 9,072,322 B2 | 7/2015 | Liu |
| 9,078,473 B2 | 7/2015 | Worm et al. |
| 9,247,773 B2 | 2/2016 | Memari et al. |
| 9,364,800 B2 | 6/2016 | Dubief |
| 9,408,416 B2 | 8/2016 | Monsees et al. |
| 9,427,022 B2 | 8/2016 | Levin et al. |
| 9,510,623 B2 | 12/2016 | Tucker et al. |
| 9,516,899 B2 | 12/2016 | Plojoux et al. |
| 9,554,597 B2 | 1/2017 | Liu |
| 9,623,592 B2 | 4/2017 | Liu |
| 9,648,909 B2 | 5/2017 | Zhou et al. |
| 9,668,521 B2 | 6/2017 | Kuczaj et al. |
| 9,668,522 B2 | 6/2017 | Memari et al. |
| 9,682,203 B2 | 6/2017 | Dähne et al. |
| 9,717,274 B2 | 8/2017 | Daehne et al. |
| 9,723,876 B2 | 8/2017 | Cadieux et al. |
| 9,770,055 B2 | 9/2017 | Cameron et al. |
| 9,772,216 B2 | 9/2017 | Poole et al. |
| 9,802,011 B2 | 10/2017 | Davidson et al. |
| 9,877,521 B1 | 1/2018 | Gillis |
| 9,949,507 B2 | 4/2018 | Flick |
| 10,058,129 B2 | 8/2018 | Monsees et al. |
| 10,064,434 B2 | 9/2018 | Zitzke et al. |
| 10,076,137 B2 | 9/2018 | Krietzman |
| 10,244,793 B2 | 4/2019 | Monsees et al. |
| 10,285,444 B2 | 5/2019 | Clemens et al. |
| 10,299,514 B2 | 5/2019 | Bilat et al. |
| 10,328,443 B2 * | 6/2019 | Ricketts ............. B05B 11/0054 |
| 10,398,169 B2 | 9/2019 | Nelson et al. |
| 10,499,690 B2 * | 12/2019 | Thorens .................. A24F 40/00 |
| 2004/0182855 A1 | 9/2004 | Centanni |
| 2005/0161467 A1 | 7/2005 | Jones |
| 2005/0172976 A1 | 8/2005 | Newman et al. |
| 2005/0236006 A1 | 10/2005 | Cowan |
| 2005/0244521 A1 | 11/2005 | Strickland et al. |
| 2005/0268909 A1 | 12/2005 | Bonney et al. |
| 2006/0191548 A1 | 8/2006 | Strickland et al. |
| 2007/0169773 A1 | 7/2007 | Rock |
| 2008/0038363 A1 | 2/2008 | Zaffaroni et al. |
| 2009/0032034 A1 | 2/2009 | Steinberg |
| 2009/0126746 A1 | 5/2009 | Strickland et al. |
| 2009/0192443 A1 | 7/2009 | Collins, Jr. |
| 2009/0230117 A1 | 9/2009 | Fernando et al. |
| 2009/0255534 A1 | 10/2009 | Paterno |
| 2009/0283103 A1 | 11/2009 | Nielsen et al. |
| 2009/0293892 A1 | 12/2009 | Williams et al. |
| 2010/0006092 A1 | 1/2010 | Hale et al. |
| 2010/0181387 A1 | 7/2010 | Zaffaroni et al. |
| 2011/0192397 A1 | 8/2011 | Saskar et al. |
| 2012/0111346 A1 | 5/2012 | Rinker et al. |
| 2012/0248005 A1 | 10/2012 | Bergey |
| 2012/0312313 A1 | 12/2012 | Frija |
| 2013/0039639 A1 | 2/2013 | Carney |
| 2013/0312742 A1 | 11/2013 | Monsees et al. |
| 2013/0327327 A1 | 12/2013 | Edwards et al. |
| 2014/0123989 A1 | 5/2014 | Lamothe |
| 2014/0150785 A1 | 6/2014 | Malik et al. |
| 2014/0178461 A1 | 6/2014 | Rigas |
| 2014/0209106 A1 | 7/2014 | Liu |
| 2014/0209107 A1 | 7/2014 | Liu |
| 2014/0261479 A1 | 9/2014 | Xu et al. |
| 2014/0261486 A1 | 9/2014 | Potter et al. |
| 2014/0262871 A1 | 9/2014 | Fath |
| 2014/0301721 A1 | 10/2014 | Ruscio et al. |
| 2014/0321837 A1 | 10/2014 | Flick |
| 2015/0013699 A1 | 1/2015 | Ellis |
| 2015/0027455 A1 | 1/2015 | Peleg et al. |
| 2015/0027456 A1 | 1/2015 | Janardhan et al. |
| 2015/0027469 A1 | 1/2015 | Tucker et al. |
| 2015/0031152 A1 | 1/2015 | Choi |
| 2015/0164147 A1 | 6/2015 | Verleur et al. |
| 2015/0223520 A1 | 8/2015 | Phillips et al. |
| 2015/0245654 A1 | 9/2015 | Memari et al. |
| 2015/0245655 A1 | 9/2015 | Memari et al. |
| 2015/0245657 A1 | 9/2015 | Memari et al. |
| 2015/0245662 A1 | 9/2015 | Memari et al. |
| 2015/0245665 A1 | 9/2015 | Memari et al. |
| 2015/0245666 A1 | 9/2015 | Memari et al. |
| 2015/0245667 A1 | 9/2015 | Memari et al. |
| 2015/0245668 A1 | 9/2015 | Memari et al. |
| 2015/0276262 A1 | 10/2015 | Dai et al. |
| 2015/0313287 A1 | 11/2015 | Verleur et al. |
| 2015/0320116 A1 | 11/2015 | Bleloch et al. |
| 2015/0328415 A1 | 11/2015 | Minskoff et al. |
| 2015/0342252 A1 | 12/2015 | Fath |
| 2015/0342256 A1 | 12/2015 | Chen |
| 2015/0359263 A1 | 12/2015 | Bellinger |
| 2015/0359264 A1 | 12/2015 | Fernando et al. |
| 2016/0021933 A1 | 1/2016 | Thorens et al. |
| 2016/0029698 A1 | 2/2016 | Xiang |
| 2016/0051716 A1 | 2/2016 | Wheelock et al. |
| 2016/0058071 A1 | 3/2016 | Hearn |
| 2016/0100632 A1 | 4/2016 | Debono et al. |
| 2016/0120222 A1 | 5/2016 | Bagai et al. |
| 2016/0135506 A1 | 5/2016 | Sanchez et al. |
| 2016/0136213 A1 | 5/2016 | Paul |
| 2016/0138795 A1 | 5/2016 | Meinhart et al. |
| 2016/0143360 A1 | 5/2016 | Sanchez et al. |
| 2016/0150824 A1 | 6/2016 | Memari et al. |
| 2016/0166564 A1 | 6/2016 | Myers et al. |
| 2016/0192705 A1 | 7/2016 | Borkovec et al. |
| 2016/0198759 A1 | 7/2016 | Kuntawala et al. |
| 2016/0213866 A1 | 7/2016 | Tan |
| 2016/0262445 A1 | 9/2016 | Benjak et al. |
| 2016/0262459 A1 | 9/2016 | Monsees et al. |
| 2016/0262526 A1 | 9/2016 | Gonzalez |
| 2016/0309789 A1 | 10/2016 | Thomas, Jr. |
| 2016/0331912 A1 | 11/2016 | Trzecieski |
| 2016/0345631 A1 | 12/2016 | Monsees et al. |
| 2016/0360790 A1 | 12/2016 | Calfee et al. |
| 2016/0374400 A1 | 12/2016 | Monsees et al. |
| 2017/0006916 A1 | 1/2017 | Liu |
| 2017/0006917 A1 | 1/2017 | Alvarez |
| 2017/0020194 A1 | 1/2017 | Rehders |
| 2017/0027234 A1 | 2/2017 | Farine et al. |
| 2017/0035109 A1 | 2/2017 | Liu |
| 2017/0064994 A1 | 3/2017 | Xu et al. |
| 2017/0071249 A1 | 3/2017 | Ampolini et al. |
| 2017/0071256 A1 | 3/2017 | Verleur et al. |
| 2017/0079329 A1 | 3/2017 | Zitzke |

(56) References Cited

U.S. PATENT DOCUMENTS

| | | | |
|---|---|---|---|
| 2017/0079331 A1 | 3/2017 | Monsees et al. | |
| 2017/0086498 A1 | 3/2017 | Daryani | |
| 2017/0086504 A1 | 3/2017 | Cameron | |
| 2017/0099877 A1 | 4/2017 | Worm et al. | |
| 2017/0105448 A1 | 4/2017 | Scarpulla | |
| 2017/0105450 A1 | 4/2017 | Reed et al. | |
| 2017/0105451 A1 | 4/2017 | Fornarelli | |
| 2017/0108210 A1 | 4/2017 | Meinhart et al. | |
| 2017/0127727 A1 | 5/2017 | Davidson et al. | |
| 2017/0135398 A1 | 5/2017 | Scott et al. | |
| 2017/0136196 A1 | 5/2017 | Davidson et al. | |
| 2017/0143041 A1 | 5/2017 | Batista et al. | |
| 2017/0144827 A1 | 5/2017 | Batista | |
| 2017/0150753 A1 | 6/2017 | Macko et al. | |
| 2017/0150755 A1 | 6/2017 | Batista | |
| 2017/0164657 A1 | 6/2017 | Batista | |
| 2017/0196268 A1 | 7/2017 | Reevell | |
| 2017/0215476 A1 | 8/2017 | Dickens et al. | |
| 2017/0231276 A1 | 8/2017 | Mironov et al. | |
| 2017/0231277 A1 | 8/2017 | Mironov et al. | |
| 2017/0231278 A1 | 8/2017 | Mironov et al. | |
| 2017/0231283 A1 | 8/2017 | Gadas | |
| 2017/0231286 A1 | 8/2017 | Borkovec et al. | |
| 2017/0245551 A1 | 8/2017 | Reevell | |
| 2017/0251714 A1 | 9/2017 | Mishra et al. | |
| 2017/0251718 A1 | 9/2017 | Armoush et al. | |
| 2017/0251723 A1 | 9/2017 | Kobal et al. | |
| 2017/0273359 A1 | 9/2017 | Liu et al. | |
| 2017/0280778 A1 | 10/2017 | Force | |
| 2017/0283154 A1 | 10/2017 | Karles et al. | |
| 2017/0295846 A1 | 10/2017 | Liu | |
| 2017/0295847 A1 | 10/2017 | Liu | |
| 2017/0333415 A1 | 11/2017 | Williams | |
| 2017/0360094 A1* | 12/2017 | Kuczaj | A61M 11/042 |
| 2018/0027883 A1 | 2/2018 | Zuber et al. | |
| 2018/0070641 A1* | 3/2018 | Batista | A61M 15/06 |
| 2018/0077967 A1 | 3/2018 | Hatton et al. | |
| 2018/0084823 A1 | 3/2018 | Fuisz et al. | |
| 2018/0110263 A1 | 4/2018 | Borkovec et al. | |
| 2018/0168227 A1 | 6/2018 | Fraser et al. | |
| 2018/0184712 A1 | 7/2018 | Fraser et al. | |
| 2018/0192700 A1 | 7/2018 | Fraser et al. | |
| 2018/0214645 A1 | 8/2018 | Reevell | |
| 2018/0271140 A1* | 9/2018 | Kobal | A24F 40/485 |
| 2018/0279682 A1 | 10/2018 | Guo et al. | |
| 2018/0296777 A1 | 10/2018 | Terry et al. | |
| 2019/0037921 A1 | 2/2019 | Kennedy et al. | |
| 2019/0124982 A1 | 5/2019 | Atkins et al. | |
| 2019/0166913 A1 | 6/2019 | Trzecieski | |
| 2019/0200677 A1* | 7/2019 | Chong | A24F 40/465 |
| 2019/0223510 A1 | 7/2019 | Bowen et al. | |
| 2020/0107585 A1 | 4/2020 | Atkins et al. | |
| 2020/0112188 A1 | 4/2020 | Cheung et al. | |
| 2020/0138117 A1 | 5/2020 | Rosser et al. | |
| 2022/0022537 A1* | 1/2022 | Murray | A24F 40/485 |
| 2022/0071289 A1* | 3/2022 | Lord | A24F 40/46 |

FOREIGN PATENT DOCUMENTS

| | | | |
|---|---|---|---|
| CN | 103929985 A | 7/2014 | |
| CN | 204180941 U | 3/2015 | |
| CN | 104770878 A | 7/2015 | |
| CN | 207023244 U | 2/2018 | |
| CN | 207285198 U | 5/2018 | |
| DE | 202018005577 U1 | 2/2019 | |
| DE | 202013012763 U1 | 5/2019 | |
| EP | 0336457 A2 | 10/1989 | |
| EP | 3178334 A1 | 6/2017 | |
| EP | 3397081 A1 | 11/2018 | |
| EP | 3423058 A1 | 1/2019 | |
| EP | 3190064 B1 | 9/2019 | |
| EP | 3248483 B1 | 9/2019 | |
| GB | 1065678 A | 4/1967 | |
| GB | 2542838 A | 4/2017 | |
| JP | H05115272 A | 5/1993 | |
| JP | 2009505649 A | 2/2009 | |
| KR | 101432877 B1 | 9/2014 | |
| KR | 101667177 B1 | 10/2016 | |
| KR | 101742249 B1 | 5/2017 | |
| KR | 20170059983 A | 5/2017 | |
| KR | 101893283 B1 | 8/2018 | |
| KR | 102016848 B1 | 8/2019 | |
| TW | 201524383 A | 7/2015 | |
| WO | WO-9712639 A1 | 4/1997 | |
| WO | WO-03082031 A1 | 10/2003 | |
| WO | WO-2006022715 A1 | 3/2006 | |
| WO | WO-2012164033 A1 | 12/2012 | |
| WO | WO-2013030202 A1 | 3/2013 | |
| WO | WO-2013089551 A1 | 6/2013 | |
| WO | WO-2014071747 A1 | 5/2014 | |
| WO | WO-2014127446 A1 | 8/2014 | |
| WO | WO-2015070405 A1 | 5/2015 | |
| WO | WO-2015150068 A1 | 10/2015 | |
| WO | WO-2015158522 A1 | 10/2015 | |
| WO | WO-2015161557 A1 | 10/2015 | |
| WO | WO-2015193456 A1 | 12/2015 | |
| WO | WO-2015196332 A1 | 12/2015 | |
| WO | WO-2015196357 A1 | 12/2015 | |
| WO | WO-2016000130 A1 | 1/2016 | |
| WO | WO-2016019353 A1 | 2/2016 | |
| WO | WO-2016029468 A1 | 3/2016 | |
| WO | WO-2016029470 A1 | 3/2016 | |
| WO | WO-2016055653 A1 | 4/2016 | |
| WO | WO-2016061730 A1 | 4/2016 | |
| WO | WO-2016082158 A1 | 6/2016 | |
| WO | WO-2016106512 A1 | 7/2016 | |
| WO | WO-2016109932 A1 | 7/2016 | |
| WO | WO-2016109942 A1 | 7/2016 | |
| WO | WO-2016115691 A1 | 7/2016 | |
| WO | WO-2016119170 A1 | 8/2016 | |
| WO | WO-2016122417 A1 | 8/2016 | |
| WO | WO-2016127397 A1 | 8/2016 | |
| WO | WO-2016127401 A1 | 8/2016 | |
| WO | WO-2016135342 A2 | 9/2016 | |
| WO | WO-2016145663 A1 | 9/2016 | |
| WO | WO-2016154895 A1 | 10/2016 | |
| WO | WO-2016161673 A1 | 10/2016 | |
| WO | WO-2016172907 A1 | 11/2016 | |
| WO | WO-2016187695 A1 | 12/2016 | |
| WO | WO-2016188140 A1 | 12/2016 | |
| WO | WO-2016188142 A1 | 12/2016 | |
| WO | WO-2016193743 A1 | 12/2016 | |
| WO | WO-2016202033 A1 | 12/2016 | |
| WO | WO-2017001352 A2 * | 1/2017 | A24F 40/42 |
| WO | WO-2017012257 A1 | 1/2017 | |
| WO | WO-2017017970 A1 | 2/2017 | |
| WO | WO-2017033021 A1 | 3/2017 | |
| WO | WO-2017036426 A3 | 3/2017 | |
| WO | WO-2017064051 A1 | 4/2017 | |
| WO | WO-2017076590 A1 | 5/2017 | |
| WO | WO-2017084849 A1 | 5/2017 | |
| WO | WO-2017109448 A2 | 6/2017 | |
| WO | WO-2017109868 A1 | 6/2017 | |
| WO | WO-2017122196 A1 | 7/2017 | |
| WO | WO-2017137510 A1 | 8/2017 | |
| WO | WO-2017141017 A1 | 8/2017 | |
| WO | WO-2017149288 A1 | 9/2017 | |
| WO | WO-2017205838 A1 | 11/2017 | |
| WO | WO-2017207416 A1 | 12/2017 | |
| WO | WO-2017207419 A1 | 12/2017 | |
| WO | WO-2017207586 A1 | 12/2017 | |
| WO | WO-2018165769 A1 | 9/2018 | |
| WO | WO-2019122015 A1 | 6/2019 | |
| WO | WO-2019232086 A1 | 12/2019 | |

* cited by examiner

CARTRIDGES FOR VAPORIZER DEVICES

CROSS-REFERENCE TO RELATED APPLICATIONS

This application claims priority to U.S. Provisional Patent Application No. 62/757,262 filed on Nov. 8, 2018, and entitled "Cartridges For Vaporizer Devices," the disclosure of which is incorporated herein by reference in its entirety.

TECHNICAL FIELD

The subject matter described herein relates to vaporizer devices, including vaporizer cartridges.

BACKGROUND

Vaporizer devices, which can also be referred to as vaporizers, electronic vaporizer devices, or e-vaporizer devices, can be used for delivery of an aerosol (for example, a vapor-phase and/or condensed-phase material suspended in a stationary or moving mass of air or some other gas carrier) containing one or more active ingredients by inhalation of the aerosol by a user of the vaporizing device. For example, electronic nicotine delivery systems (ENDS) include a class of vaporizer devices that are battery powered and that can be used to simulate the experience of smoking, but without burning of tobacco or other substances. Vaporizer devices are gaining increasing popularity both for prescriptive medical use, in delivering medicaments, and for consumption of tobacco, nicotine, and other plant-based materials. Vaporizer devices can be portable, self-contained, and/or convenient for use.

In use of a vaporizer device, the user inhales an aerosol, colloquially referred to as "vapor," which can be generated by a heating element that vaporizes (e.g., causes a liquid or solid to at least partially transition to the gas phase) a vaporizable material, which can be liquid, a solution, a solid, a paste, a wax, and/or any other form compatible for use with a specific vaporizer device. The vaporizable material used with a vaporizer device can be provided within a cartridge for example, a separable part of the vaporizer device that contains vaporizable material) that includes an outlet (for example, a mouthpiece) for inhalation of the aerosol by a user.

To receive the inhalable aerosol generated by a vaporizer device, a user may, in certain examples, activate the vaporizer device by taking a puff, by pressing a button, and/or by some other approach. A puff as used herein can refer to inhalation by the user in a manner that causes a volume of air to be drawn into the vaporizer device such that the inhalable aerosol is generated by a combination of the vaporized vaporizable material with the volume of air.

An approach by which a vaporizer device generates an inhalable aerosol from a vaporizable material involves heating the vaporizable material in a vaporization chamber (e.g., a heater chamber) to cause the vaporizable material to be converted to the gas (or vapor) phase. A vaporization chamber can refer to an area or volume in the vaporizer device within which a heat source (for example, a conductive, convective, and/or radiative heat source) causes heating of a vaporizable material to produce a mixture of air and vaporized material to form a vapor for inhalation of the vaporizable material by a user of the vaporizer device.

Vaporizer devices can be controlled by one or more controllers, electronic circuits (for example, sensors, heating elements), and/or the like on the vaporizer device. Vaporizer devices can also wirelessly communicate with an external controller for example, a computing device such as a smartphone).

In various implementations, a vaporizer device may be configured for use with liquid vaporizable material (e.g., a carrier solution in which an active and/or inactive ingredient(s) are suspended or held in solution or a neat liquid form of the vaporizable material itself). In such instances, the liquid vaporizable material can be stored within a reservoir of the device (or of a cartridge for use with the device). However, a free liquid reservoir has a potential to leak.

Vaporizable material leaks are problematic because such leaks typically interfere with the functionality and cleanliness of the vaporizer device (e.g., leaked vaporizable material plugs the electric ports or makes a mess that requires cleaning). Additionally, user experience is negatively impacted by leakage of vaporizable material from a cartridge due to the possibility of staining or damaging other articles or fabrics adjacent to a leaking cartridge. Leaks into certain parts of a cartridge or a vaporizer device may also result in liquid vaporizable material bypassing an atomizer configured to convert the liquid vaporizable material to vapor or aerosol form, thereby causing a user to experience unpleasant sensations from inhaling the vaporizable material in the liquid form.

Alternatively, the liquid vaporizable material can be absorbed into and stored within a porous material. However, when using a porous material as a storage medium, inconsistent dosing of the liquid vaporizable material over the lifetime of the vaporizer device can lead to challenges around volumetric efficiency and can also result in poor delivery characteristics.

Accordingly, vaporization devices and/or vaporization cartridges that address one or more of these issues are desired.

SUMMARY

Aspects of the current subject matter relate to vaporizer devices and to cartridges for use in a vaporizer device.

In some variations, one or more of the following features may optionally be included in any feasible combination.

In one exemplary embodiment, a cartridge is provided and includes a reservoir configured to contain a plurality of encapsulated particles and an airflow tube extending through the reservoir. Each of the plurality of encapsulated particles includes a core formed of a liquid vaporizable material and a coating material that forms a shell surrounding the core, in which the shells of the plurality of encapsulated particles are configured to be selectively ruptured to release the liquid vaporizable material therefrom. The airflow tube includes a wicking element that is in communication with the reservoir, in which the wicking element is configured to draw, into the airflow tube for vaporization, at least a portion of the liquid vaporizable material that is released by rupturing one or more shells of the plurality of encapsulated particles.

In some embodiments, the wicking element can be configured to substantially draw at least a portion of ruptured shells into the airflow tube for vaporization. In such embodiments, the vaporization of the portion of the ruptured shells drawn into the airflow tube can occur concurrently with the vaporization of the liquid vaporizable material.

In some embodiments, the wicking element can be configured to be selectively bulk heated to thermally rupture a portion of the shells of the plurality of encapsulated particles to release the liquid vaporizable material therefrom. In such embodiments, the portion of the shells that are ruptured can be within a predetermined distance of the wicking element.

In some embodiments, the wicking element can be configured to receive at least a portion of the released liquid vaporizable material under the influence of gravity.

The reservoir can have a variety of configurations. For example, in some embodiments, the reservoir can include at least one vent that can be configured to substantially allow air to pass into the reservoir. The at least one vent can be configured to inhibit the plurality of encapsulated particles to pass therethrough and out of the reservoir.

The shells of the plurality of encapsulated particles can have a variety of configurations. For example, in some embodiments, the shells of the plurality of the encapsulated particles can be configured to be thermally ruptured. In other embodiments, the shells of the plurality of encapsulated particles can be configured to be mechanically ruptured. In yet other embodiments, the shells of the plurality of encapsulated particles can be configured to be chemically ruptured.

In another exemplary embodiment, a cartridge is provided and includes a reservoir configured to contain a plurality of particles and an airflow tube extending through the reservoir. Each particle of the plurality of particles is formed of a substantially solid vaporizable material. The airflow tube includes a wicking element that is in communication with the reservoir, in which the wicking element is configured to be selectively bulk heated to cause a portion of the plurality of particles to be substantially melted to form a liquid vaporizable material, and in which the wicking element is configured to draw the liquid vaporizable material into the airflow tube for vaporization.

In some embodiments, the wicking element can be configured to receive at least a portion of the liquid vaporizable material under the influence of gravity.

The reservoir can have a variety of configurations. For example, in some embodiments, the reservoir can include at least one vent that can be configured to substantially allow air to pass into the reservoir. The at least one vent can be configured to substantially inhibit the plurality of particles to pass therethrough and out of the reservoir.

In some embodiments, the portion of the plurality of particles that are substantially melted can be within a predetermined distance of the wicking element.

In another exemplary embodiment, a vaporizer device is provided and includes a vaporizer body and a cartridge that is selectively coupled to and removable from the vaporizer body. The cartridge includes a reservoir configured to contain a plurality of encapsulated particles and an airflow tube extending through the reservoir. Each of the plurality of encapsulated particles includes a core formed of a liquid vaporizable material and a coating material that forms a shell surrounding the core, in which the shells of the plurality of encapsulated particles are configured to be selectively ruptured to release the liquid vaporizable material therefrom. The airflow tube includes a wicking element that is in communication with the reservoir, in which the wicking element is configured to draw, into the airflow tube for vaporization, at least a portion of the liquid vaporizable material that is released by rupturing one or more shells of the plurality of encapsulated particles.

The shells of the plurality of encapsulated particles can have a variety of configurations. For example, in some embodiments, the shells of the plurality of encapsulated particles can be configured to be at least one of thermally ruptured, mechanically ruptured, or chemically ruptured.

In some embodiments, the wicking element can be configured to be selectively bulk heated to thermally rupture a portion of the shells of the plurality of encapsulated particles to release the liquid vaporizable material therefrom.

In some embodiments, the wicking element can be configured to receive at least a portion of the released liquid vaporizable material under the influence of gravity.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

BRIEF DESCRIPTION OF THE DRAWINGS

The accompanying drawings, which are incorporated into and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Implementations of the current subject matter include methods, apparatuses, articles of manufacture, and systems relating to vaporization of one or more materials for inhalation by a user. Example implementations include vaporizer devices and systems including vaporizer devices. The term "vaporizer device" as used in the following description and claims refers to any of a self-contained apparatus, an apparatus that includes two or more separable parts (for example, a vaporizer body that includes a battery and other hardware, and a cartridge that includes a vaporizable material), and/or the like. A "vaporizer system," as used herein, can include one or more components, such as a vaporizer device. Examples of vaporizer devices consistent with implementations of the current subject matter include electronic vaporizers, electronic nicotine delivery systems (ENDS), and/or the like. In general, such vaporizer devices are hand-held devices that heat (such as by convection, conduction, radiation, and/or some combination thereof) a vaporizable material to provide an inhalable dose of the material.

The vaporizable material used with a vaporizer device can be provided within a cartridge (for example, a part of the vaporizer device that contains the vaporizable material in a reservoir or other container) which can be refillable when empty, or disposable such that a new cartridge containing additional vaporizable material of a same or different type can be used). A vaporizer device can be a cartridge-using vaporizer device, a cartridge-less vaporizer device, or a multi-use vaporizer device capable of use with or without a cartridge. For example, a vaporizer device can include a heating chamber (for example, an oven or other region in which material is heated by a heating element) configured to receive a vaporizable material directly into the heating chamber, and/or a reservoir or the like for containing the vaporizable material.

In some implementations, a vaporizer device can be configured for use with a liquid vaporizable material (for example, a carrier solution in which an active and/or inactive ingredient(s) are suspended or held in solution, or a liquid form of the vaporizable material itself). The liquid vaporizable material can be capable of being completely vaporized. Alternatively, at least a portion of the liquid vaporizable material can remain after all of the material suitable for inhalation has been vaporized.

Figure 1A:
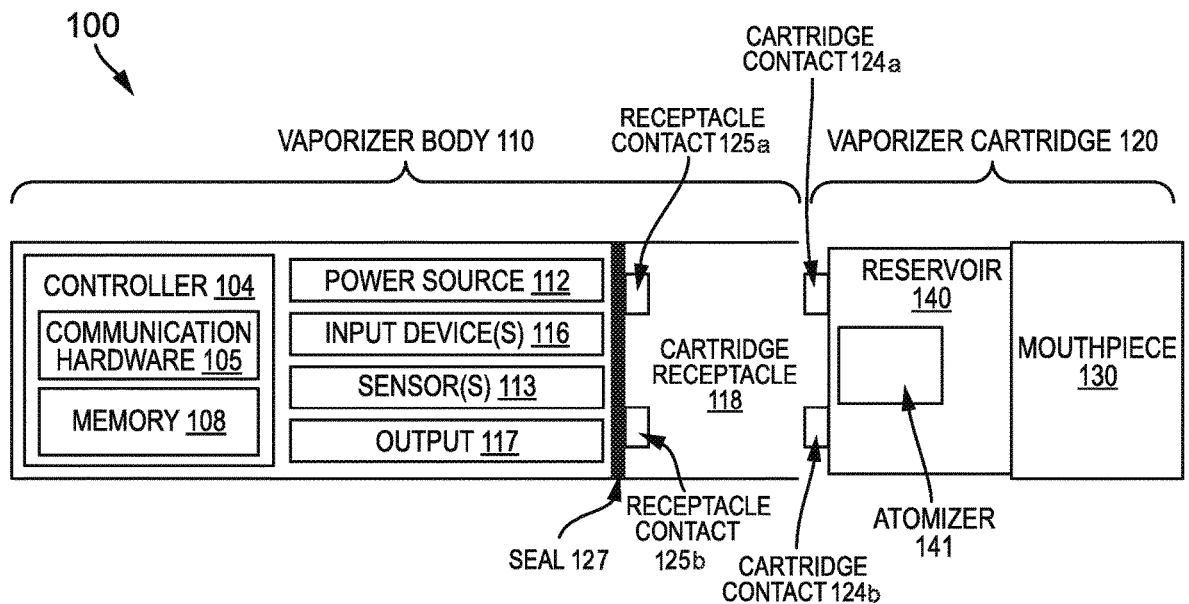
FIG. 1A is a block diagram of a vaporizer device.

Referring to the block diagram of FIG. 1A, a vaporizer device 100 can include a power source 112 (for example, a battery, which can be a rechargeable battery), and a controller 104 (for example, a processor, circuitry, etc. capable of executing logic) for controlling delivery of heat to an atomizer 141 to cause a vaporizable material 102 to be converted from a condensed form (such as a liquid, a solution, a suspension, a part of an at least partially unprocessed plant material, etc.) to the gas phase. The controller 104 can be part of one or more printed circuit boards (PCBs) consistent with certain implementations of the current subject matter.

After conversion of the vaporizable material 102 to the gas phase, at least some of the vaporizable material 102 in the gas phase can condense to form particulate matter in at least a partial local equilibrium with the gas phase as part of an aerosol, which can form some or all of an inhalable dose provided by the vaporizer device 100 during a user's puff or draw on the vaporizer device 100. It should be appreciated that the interplay between gas and condensed phases in an aerosol generated by a vaporizer device 100 can be complex and dynamic, due to factors such as ambient temperature, relative humidity, chemistry, flow conditions in airflow paths (both inside the vaporizer device and in the airways of a human or other animal), and/or mixing of the vaporizable material 102 in the gas phase or in the aerosol phase with other air streams, which can affect one or more physical parameters of an aerosol. In some vaporizer devices, and particularly for vaporizer devices configured for delivery of volatile vaporizable materials, the inhalable dose can exist predominantly in the gas phase (for example, formation of condensed phase particles can be very limited).

The atomizer 141 in the vaporizer device 100 can be configured to vaporize a vaporizable material 102. The vaporizable material 102 can be a liquid. Examples of the vaporizable material 102 include neat liquids, suspensions, solutions, mixtures, and/or the like. The atomizer 141 can include a wicking element (i.e., a wick) configured to convey an amount of the vaporizable material 102 to a part of the atomizer 141 that includes a heating element (not shown in FIG. 1A).

For example, the wicking element can be configured to draw the vaporizable material 102 from a reservoir 140 configured to contain the vaporizable material 102, such that the vaporizable material 102 can be vaporized by heat delivered from a heating element. The wicking element can also optionally allow air to enter the reservoir 140 and replace the volume of vaporizable material 102 removed. In some implementations of the current subject matter, capillary action can pull vaporizable material 102 into the wick for vaporization by the heating element, and air can return to the reservoir 140 through the wick to at least partially equalize pressure in the reservoir 140. Other methods of allowing air back into the reservoir 140 to equalize pressure are also within the scope of the current subject matter.

As used herein, the terms "wick" or "wicking element" include any material capable of causing fluid motion via capillary pressure.

The heating element can include one or more of a conductive heater, a radiative heater, and/or a convective heater. One type of heating element is a resistive heating element, which can include a material (such as a metal or alloy, for example a nickel-chromium alloy, or a non-metallic resistor) configured to dissipate electrical power in the form of heat when electrical current is passed through one or more resistive segments of the heating element. In some implementations of the current subject matter, the atomizer 141 can include a heating element which includes a resistive coil or other heating element wrapped around, positioned within, integrated into a bulk shape of, pressed into thermal contact with, or otherwise arranged to deliver heat to a wicking element, to cause the vaporizable material 102 drawn from the reservoir 140 by the wicking element to be vaporized for subsequent inhalation by a user in a gas and/or a condensed (for example, aerosol particles or droplets) phase. Other wicking elements, heating elements, and/or atomizer assembly configurations are also possible.

The heating element can be activated in association with a user puffing (i.e., drawing, inhaling, etc.) on a mouthpiece 130 of the vaporizer device 100 to cause air to flow from an air inlet, along an airflow path that passes the atomizer 141 (i.e., wicking element and heating element). Optionally, air can flow from an air inlet through one or more condensation areas or chambers, to an air outlet in the mouthpiece 130. Incoming air moving along the airflow path moves over or through the atomizer 141, where vaporizable material 102 in the gas phase is entrained into the air. The heating element can be activated via the controller 104, which can optionally be a part of a vaporizer body 110 as discussed herein, causing current to pass from the power source 112 through a circuit including the resistive heating element, which is optionally part of a vaporizer cartridge 120 as discussed herein. As noted herein, the entrained vaporizable material 102 in the gas phase can condense as it passes through the remainder of the airflow path such that an inhalable dose of the vaporizable material 102 in an aerosol form can be delivered from the air outlet (for example, the mouthpiece 130) for inhalation by a user.

Activation of the heating element can be caused by automatic detection of a puff based on one or more signals generated by one or more of a sensor 113. The sensor 113 and the signals generated by the sensor 113 can include one or more of: a pressure sensor or sensors disposed to detect pressure along the airflow path relative to ambient pressure (or optionally to measure changes in absolute pressure), a motion sensor or sensors (for example, an accelerometer) of the vaporizer device 100, a flow sensor or sensors of the vaporizer device 100, a capacitive lip sensor of the vaporizer device 100, detection of interaction of a user with the vaporizer device 100 via one or more input devices 116 (for example, buttons or other tactile control devices of the vaporizer device 100), receipt of signals from a computing device in communication with the vaporizer device 100, and/or via other approaches for determining that a puff is occurring or imminent.

As discussed herein, the vaporizer device 100 consistent with implementations of the current subject matter can be configured to connect (such as, for example, wirelessly or via a wired connection) to a computing device (or optionally two or more devices) in communication with the vaporizer device 100. To this end, the controller 104 can include communication hardware 105. The controller 104 can also include a memory 108. The communication hardware 105 can include firmware and/or can be controlled by software for executing one or more cryptographic protocols for the communication.

A computing device can be a component of a vaporizer system that also includes the vaporizer device 100, and can include its own hardware for communication, which can establish a wireless communication channel with the communication hardware 105 of the vaporizer device 100. For example, a computing device used as part of a vaporizer system can include a general-purpose computing device (such as a smartphone, a tablet, a personal computer, some other portable device such as a smartwatch, or the like) that executes software to produce a user interface for enabling a user to interact with the vaporizer device 100. In other implementations of the current subject matter, such a device used as part of a vaporizer system can be a dedicated piece of hardware such as a remote control or other wireless or wired device having one or more physical or soft (i.e., configurable on a screen or other display device and selectable via user interaction with a touch-sensitive screen or some other input device like a mouse, pointer, trackball, cursor buttons, or the like) interface controls. The vaporizer device 100 can also include one or more outputs 117 or devices for providing information to the user. For example, the outputs 117 can include one or more light emitting diodes (LEDs) configured to provide feedback to a user based on a status and/or mode of operation of the vaporizer device 100.

In the example in which a computing device provides signals related to activation of the resistive heating element, or in other examples of coupling of a computing device with the vaporizer device 100 for implementation of various control or other functions, the computing device executes one or more computer instruction sets to provide a user interface and underlying data handling. In one example, detection by the computing device of user interaction with one or more user interface elements can cause the computing device to signal the vaporizer device 100 to activate the heating element to reach an operating temperature for creation of an inhalable dose of vapor/aerosol. Other functions of the vaporizer device 100 can be controlled by interaction of a user with a user interface on a computing device in communication with the vaporizer device 100.

The temperature of a resistive heating element of the vaporizer device 100 can depend on a number of factors, including an amount of electrical power delivered to the resistive heating element and/or a duty cycle at which the electrical power is delivered, conductive heat transfer to other parts of the electronic vaporizer device 100 and/or to the environment, latent heat losses due to vaporization of the vaporizable material 102 from the wicking element and/or the atomizer 141 as a whole, and convective heat losses due to airflow (i.e., air moving across the heating element or the atomizer 141 as a whole when a user inhales on the vaporizer device 100). As noted herein, to reliably activate the heating element or heat the heating element to a desired temperature, the vaporizer device 100 may, in some implementations of the current subject matter, make use of signals from the sensor 113 (for example, a pressure sensor) to determine when a user is inhaling. The sensor 113 can be positioned in the airflow path and/or can be connected (for example, by a passageway or other path) to an airflow path containing an inlet for air to enter the vaporizer device 100 and an outlet via which the user inhales the resulting vapor and/or aerosol such that the sensor 113 experiences changes (for example, pressure changes) concurrently with air passing through the vaporizer device 100 from the air inlet to the air outlet. In some implementations of the current subject matter, the heating element can be activated in association with a user's puff, for example by automatic detection of the puff, or by the sensor 113 detecting a change (such as a pressure change) in the airflow path.

The sensor 113 can be positioned on or coupled to (i.e., electrically or electronically connected, either physically or via a wireless connection) the controller 104 (for example, a printed circuit board assembly or other type of circuit board). To take measurements accurately and maintain durability of the vaporizer device 100, it can be beneficial to provide a seal 127 resilient enough to separate an airflow path from other parts of the vaporizer device 100. The seal 127, which can be a gasket, can be configured to at least partially surround the sensor 113 such that connections of the sensor 113 to the internal circuitry of the vaporizer device 100 are separated from a part of the sensor 113 exposed to the airflow path. In an example of a cartridge-based vaporizer device, the seal 127 can also separate parts of one or more electrical connections between the vaporizer body 110 and the vaporizer cartridge 120. Such arrangements of the seal 127 in the vaporizer device 100 can be helpful in mitigating against potentially disruptive impacts on vaporizer components resulting from interactions with environmental factors such as water in the vapor or liquid phases, other fluids such as the vaporizable material 102, etc., and/or to reduce the escape of air from the designated airflow path in the vaporizer device 100. Unwanted air, liquid or other fluid passing and/or contacting circuitry of the vaporizer device 100 can cause various unwanted effects, such as altered pressure readings, and/or can result in the buildup of unwanted material, such as moisture, excess vaporizable material 102, etc., in parts of the vaporizer device 100 where they can result in poor pressure signal, degradation of the sensor 113 or other components, and/or a shorter life of the vaporizer device 100. Leaks in the seal 127 can also result in a user inhaling air that has passed over parts of the vaporizer device 100 containing, or constructed of, materials that may not be desirable to be inhaled.

In some implementations, the vaporizer body 110 includes the controller 104, the power source 112 (for example, a battery), one more of the sensor 113, charging contacts (such as those for charging the power source 112), the seal 127, and a cartridge receptacle 118 configured to receive the vaporizer cartridge 120 for coupling with the vaporizer body 110 through one or more of a variety of attachment structures. In some examples, the vaporizer cartridge 120 includes the reservoir 140 for containing the vaporizable material 102, and the mouthpiece 130 has an aerosol outlet for delivering an inhalable dose to a user. The vaporizer cartridge 120 can include the atomizer 141 having a wicking element and a heating element. Alternatively, one or both of the wicking element and the heating element can be part of the vaporizer body 110. In implementations in which any part of the atomizer 141 (i.e., heating element and/or wicking element) is part of the vaporizer body 110, the vaporizer device 100 can be configured to supply vaporizable material 102 from the reservoir 140 in the vaporizer cartridge 120 to the part(s) of the atomizer 141 included in the vaporizer body 110.

In an embodiment of the vaporizer device 100 in which the power source 112 is part of the vaporizer body 110, and a heating element is disposed in the vaporizer cartridge 120 and configured to couple with the vaporizer body 110, the vaporizer device 100 can include electrical connection features (for example, means for completing a circuit) for completing a circuit that includes the controller 104 (for example, a printed circuit board, a microcontroller, or the like), the power source 112, and the heating element (for example, a heating element within the atomizer 141). These features can include one or more contacts (referred to herein as cartridge contacts 124a and 124b) on a bottom surface of the vaporizer cartridge 120 and at least two contacts (referred to herein as receptacle contacts 125a and 125b) disposed near a base of the cartridge receptacle 118 of the vaporizer device 100 such that the cartridge contacts 124a and 124b and the receptacle contacts 125a and 125b make electrical connections when the vaporizer cartridge 120 is inserted into and coupled with the cartridge receptacle 118. The circuit completed by these electrical connections can allow delivery of electrical current to a heating element and can further be used for additional functions, such as measuring a resistance of the heating element for use in determining and/or controlling a temperature of the heating element based on a thermal coefficient of resistivity of the heating element.

In some implementations of the current subject matter, the cartridge contacts 124a and 124b and the receptacle contacts 125a and 125b can be configured to electrically connect in either of at least two orientations. In other words, one or more circuits necessary for operation of the vaporizer device 100 can be completed by insertion of the vaporizer cartridge 120 into the cartridge receptacle 118 in a first rotational orientation (around an axis along which the vaporizer cartridge 120 is inserted into the cartridge receptacle 118 of the vaporizer body 110) such that the cartridge contact 124a is electrically connected to the receptacle contact 125a and the cartridge contact 124b is electrically connected to the receptacle contact 125b. Furthermore, the one or more circuits necessary for operation of the vaporizer device 100 can be completed by insertion of the vaporizer cartridge 120 in the cartridge receptacle 118 in a second rotational orientation such cartridge contact 124a is electrically connected to the receptacle contact 125b and cartridge contact 124b is electrically connected to the receptacle contact 125a.

For example, the vaporizer cartridge 120 or at least the insertable end 122 of the vaporizer cartridge 120 can be symmetrical upon a rotation of 180° around an axis along which the vaporizer cartridge 120 is inserted into the cartridge receptacle 118. In such a configuration, the circuitry of the vaporizer device 100 can support identical operation regardless of which symmetrical orientation of the vaporizer cartridge 120 occurs.

In one example of an attachment structure for coupling the vaporizer cartridge 120 to the vaporizer body 110, the vaporizer body 110 includes one or more detents (for example, dimples, protrusions, etc.) protruding inwardly from an inner surface of the cartridge receptacle 118, additional material (such as metal, plastic, etc.) formed to include a portion protruding into the cartridge receptacle 118, and/or the like. One or more exterior surfaces of the vaporizer cartridge 120 can include corresponding recesses (not shown in FIG. 1A) that can fit and/or otherwise snap over such detents or protruding portions when the vaporizer cartridge 120 is inserted into the cartridge receptacle 118 on the vaporizer body 110. When the vaporizer cartridge 120 and the vaporizer body 110 are coupled (e.g., by insertion of the vaporizer cartridge 120 into the cartridge receptacle 118 of the vaporizer body 110), the detents or protrusions of the vaporizer body 110 can fit within and/or otherwise be held within the recesses of the vaporizer cartridge 120, to hold the vaporizer cartridge 120 in place when assembled. Such an assembly can provide enough support to hold the vaporizer cartridge 120 in place to ensure good contact between the cartridge contacts 124a and 124b and the receptacle contacts 125a and 125b, while allowing release of the vaporizer cartridge 120 from the vaporizer body 110 when a user pulls with reasonable force on the vaporizer cartridge 120 to disengage the vaporizer cartridge 120 from the cartridge receptacle 118.

In some implementations, the vaporizer cartridge 120, or at least an insertable end 122 of the vaporizer cartridge 120 configured for insertion in the cartridge receptacle 118, can have a non-circular cross section transverse to the axis along which the vaporizer cartridge 120 is inserted into the cartridge receptacle 118. For example, the non-circular cross section can be approximately rectangular, approximately elliptical (i.e., have an approximately oval shape), non-rectangular but with two sets of parallel or approximately parallel opposing sides (i.e., having a parallelogram-like shape), or other shapes having rotational symmetry of at least order two. In this context, approximate shape indicates that a basic likeness to the described shape is apparent, but that sides of the shape in question need not be completely linear and vertices need not be completely sharp. Rounding of both or either of the edges or the vertices of the cross-sectional shape is contemplated in the description of any non-circular cross section referred to herein.

The cartridge contacts 124a and 124b and the receptacle contacts 125a and 125b can take various forms. For example, one or both sets of contacts can include conductive pins, tabs, posts, receiving holes for pins or posts, or the like. Some types of contacts can include springs or other features to facilitate better physical and electrical contact between the contacts on the vaporizer cartridge 120 and the vaporizer body 110. The electrical contacts can optionally be gold-plated, and/or include other materials.

Figure 1B:
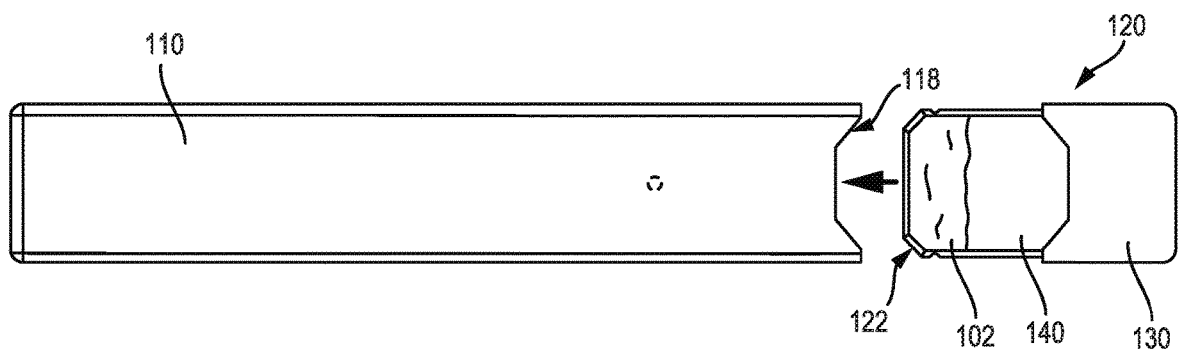
FIG. 1B is a top view of an embodiment of a vaporizer device, showing a vaporizer cartridge separated from a vaporizer device body.
Figure 1C:
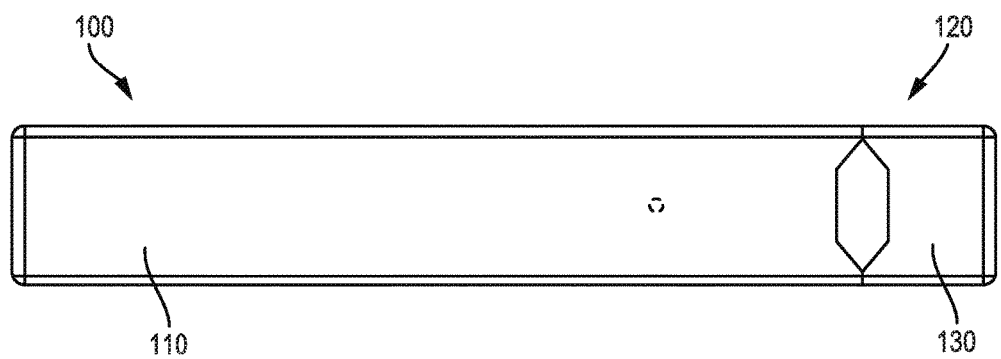
FIG. 1C is a top view of the vaporizer device of FIG. 1B, showing the vaporizer cartridge coupled to the vaporizer device body.
Figure 1D:
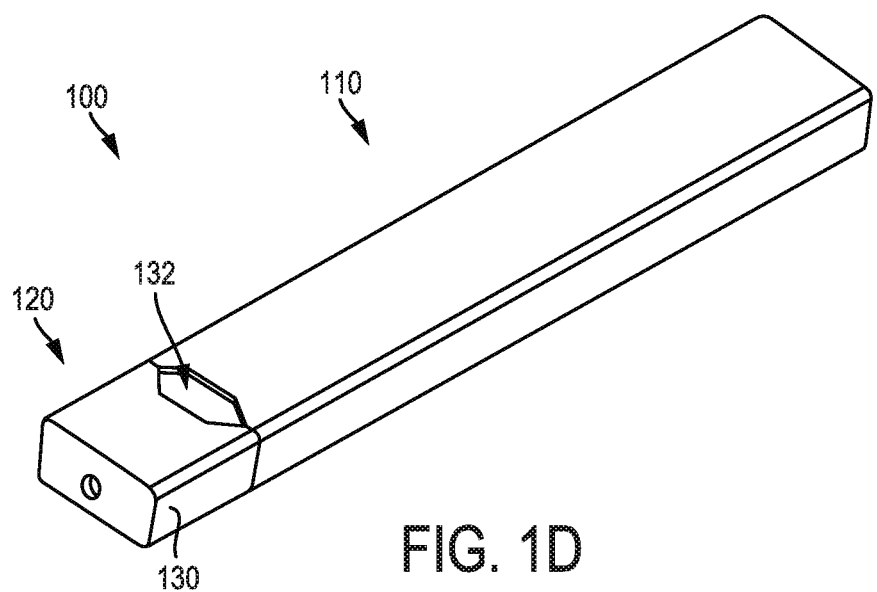
FIG. 1D is a perspective view of the vaporizer device of FIG. 1C.

FIGS. 1B-1D illustrate an embodiment of the vaporizer body 110 having a cartridge receptacle 118 into which the vaporizer cartridge 120 can be releasably inserted. FIGS. 1B and 1C show top views of the vaporizer device 100 illustrating the vaporizer cartridge 120 being positioned for insertion and inserted, respectively, into the vaporizer body 110. FIG. 1D illustrates the reservoir 140 of the vaporizer cartridge 120 being formed in whole or in part from translucent material such that a level of the vaporizable material 102 is visible from a window 132 (e.g., translucent material) along the vaporizer cartridge 120. The vaporizer cartridge 120 can be configured such that the window 132 remains visible when insertably received by the vaporizer cartridge receptacle 118 of the vaporizer body 110. For example, in one exemplary configuration, the window 132 can be disposed between a bottom edge of the mouthpiece 130 and a top edge of the vaporizer body 110 when the vaporizer cartridge 120 is coupled with the cartridge receptacle 118.

Figure 1E:
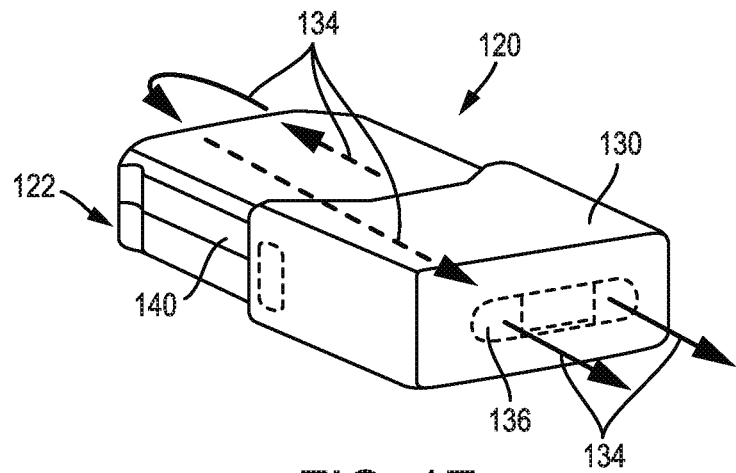
FIG. 1E is a perspective view of the vaporizer cartridge of FIG. 1B.

FIG. 1E illustrates an example airflow path 134 created during a puff by a user on the vaporizer device 100. The airflow path 134 can direct air to a vaporization chamber 150 (see FIG. 1F) contained in a wick housing where the air is combined with inhalable aerosol for delivery to a user via a mouthpiece 130, which can also be part of the vaporizer cartridge 120. For example, when a user puffs on the vaporizer device 100 device 100, air can pass between an outer surface of the vaporizer cartridge 120 (for example, window 132 shown in FIG. 1D) and an inner surface of the cartridge receptacle 118 on the vaporizer body 110. Air can then be drawn into the insertable end 122 of the vaporizer cartridge 120, through the vaporization chamber 150 that includes or contains the heating element and wick, and out through an outlet 136 of the mouthpiece 130 for delivery of the inhalable aerosol to a user.

As shown in FIG. 1E, this configuration causes air to flow down around the insertable end 122 of the vaporizer cartridge 120 into the cartridge receptacle 118 and then flow back in the opposite direction after passing around the insertable end 122 (e.g., an end opposite of the end including the mouthpiece 130) of the vaporizer cartridge 120 as it enters into the cartridge body toward the vaporization chamber 150. The airflow path 134 then travels through the interior of the vaporizer cartridge 120, for example via one or more tubes or internal channels (such as cannula 128 shown in FIG. 1F) and through one or more outlets (such as outlet 136) formed in the mouthpiece 130. The mouthpiece 130 can be a separable component of the vaporizer cartridge 120 or can be integrally formed with other component(s) of the vaporizer cartridge 120 (for example, formed as a unitary structure with the reservoir 140 and/or the like).

Figure 1F:
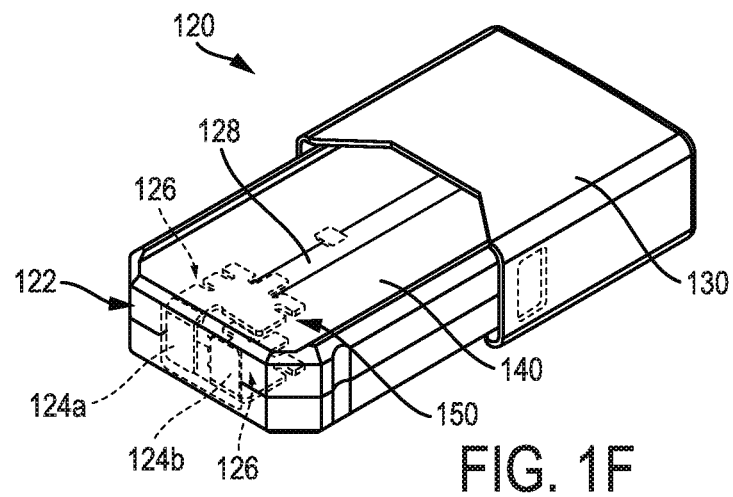
FIG. 1F is another perspective view of the vaporizer cartridge of FIG. 1E.

FIG. 1F shows additional features that can be included in the vaporizer cartridge 120 consistent with implementations of the current subject matter. For example, the vaporizer cartridge 120 can include a plurality of cartridge contacts (such as cartridge contacts 124a, 124b) disposed on the insertable end 122. The cartridge contacts 124a, 124b can optionally each be part of a single piece of metal that forms a conductive structure (such as conductive structure 126) connected to one of two ends of a resistive heating element. The conductive structure can optionally form opposing sides of a heating chamber and can act as heat shields and/or heat sinks to reduce transmission of heat to outer walls of the vaporizer cartridge 120. FIG. 1F also shows the cannula 128 within the vaporizer cartridge 120 that defines part of the airflow path 134 between the heating chamber formed between the conductive structure 126 and the mouthpiece 130.

As mentioned above, storing a liquid vaporizable material within a free liquid reservoir can result in undesirable leakage. Further, when using a porous material as a storage medium for the liquid vaporizable material, challenges with volumetric efficiency and poor delivery characteristics can result. Various features and devices are described below that improve upon or overcome storage issues of vaporizable material.

The vaporizer cartridges described herein are designed to store a plurality of particles of vaporizable material in a reservoir in which the particles are configured to be selectively melted or ruptured in response to an event (e.g., heating, mechanical interaction, chemical interaction, and the like). The melting or rupturing of these particles are configured to provide an on-demand delivery of liquid vaporizable material to form a vapor for inhalation by a user of a vaporization device. On-demand delivery of liquid vaporizable material for vaporization through melting or rupturing of particles inhibits undesirable leakage and provides the ability to use a storage medium that can effectively delivery liquid vaporizable material throughout the lifetime of the vaporizer cartridge.

The cartridges generally include a reservoir and an airflow tube that includes a wicking element that is in communication with the reservoir. The reservoir is configured to contain a plurality of particles that contain a volume of a vaporizable material. The plurality of particles can have any suitable particle size (e.g., from about 10 nm to 1 mm, or other sizes that achieve one or more advantages as described herein). The distribution of the plurality of particles within the reservoir can adopt any desired distribution such as, for example, Gaussian, multi-modal, and/or the like.

The wicking element is configured to at least draw a portion of a liquid vaporizable material into the airflow tube for vaporization. The wicking element can be formed of any suitable material that can draw the liquid vaporizable material in the airflow tube, e.g., by capillary action. Non-limiting examples of suitable materials for the wicking element can include of one or more ceramic materials, one or more cottons, or one or more polymers. In one embodiment, the wicking element is formed of one or more ceramic materials.

Such drawing of the liquid vaporizable material into the airflow tube can be due, at least in part, to capillary action provided by the wicking element, which pulls the vaporizable material along the wick in the direction of the airflow tube. As discussed in more detail below, the liquid vaporizable material is formed by selectively melting or rupturing of some amount of the plurality of particles. In one embodiment, the wicking element can also be configured to receive at least a portion of the liquid vaporizable material under the influence of gravity.

In some embodiments, the plurality of particles can be in the form of encapsulated particles that include a core and a coating material that forms a shell about the core. The core is formed of a liquid vaporizable material. The shells are configured to be selectively ruptured within the cartridge to release the liquid vaporizable material therefrom such that the wicking element can draw a portion thereof into the airflow tube for vaporization. The coating material can be any suitable material that can effectively form a shell that can house the liquid vaporizable material described herein while also being capable of being selectively ruptured when desired. The encapsulated particles can be formed using any known suitable encapsulation method.

In some embodiments, the wicking element can be further configured to substantially draw at least a portion of ruptured shells into the airflow tube for vaporization. In one embodiment, the vaporization of the portion of the ruptured shells drawn into the airflow tube occurs concurrently with the vaporization of the liquid vaporizable material.

The shells can be configured to be thermally ruptured, mechanically ruptured, chemically ruptured, or any combination thereof.

In some embodiments, the shells can be thermally ruptured in response to bulk heating of the wicking element. For example, the heated wicking element can dissipate heat into the reservoir to which at least a portion of the plurality of encapsulated particles are exposed thereto. The portion of the shells that are exposed to the heat can be within a predetermined distance of the wicking element. This heat exposure can cause the exposed shells of the plurality of encapsulated particles to substantially melt, thereby releasing their respective portions of the liquid vaporizable material. The released liquid vaporizable material can be drawn into the wicking element, and ultimately vaporized into vaporized material.

The wicking element can be bulk heated using any suitable known technique. For example, the wicking element can be heated via ohmic heating, capacitive heating, and the like. In one embodiment, the wicking element can be heated by a separate heating element. In another embodiment, the wicking element can be heated in response to receiving an electric current itself from a power source. In yet another embodiment, the wicking element can be heated in response to an electrical potential being created across it (e.g., between two metal plates on opposing sides of the wicking element).

In some embodiments, the shells can be mechanically ruptured, for example, by coming into contact with at least one surface of the wicking element that is roughened, e.g., to include one or more spikes, or other abrasive features, etc., so that the shells of the encapsulated particles rupture upon coming into contact with at least a portion of such roughened surface. Alternatively, or in addition, at least a portion of the inner surface of the reservoir can be roughened, e.g., to include one or more spikes, or other abrasive features, etc., so that the shells of the encapsulated particles rupture upon coming into contact with at least a portion of the roughened surface of the reservoir.

In some embodiments, the shells can be chemically ruptured by coming into contact with the wicking element itself. For example, the wicking element can be formed of a material that is configured to chemically interact with the shells such that at least a portion of the shells breakdown, and therefore release their respective portions of the liquid vaporizable material therefrom. Alternatively, or in addition thereto, the shells can come into contact with an interference material that is configured to chemically interact with, and cause the breakdown of, the shells. The interference material can be added directly to or in close proximity with the wicking element.

In other embodiments, the plurality of particles can be in the form of substantially solid vaporizable material that are configured to be selectively melted to form a liquid vaporizable material such that the wicking element can draw a portion thereof into the airflow tube for vaporization. In some embodiments, the substantially solid vaporizable material can be substantially melted in response to bulk heating of the wicking element, such as the bulk heating discussed above. For example, the heated wicking element can dissipate heat into the reservoir to which at least a portion of the plurality of particles are exposed thereto. The portion of the particles that are exposed to the heat can be within a predetermined distance of the wicking element. This heat exposure can cause the exposed particles to substantially melt, thereby undergoing a phase change to form liquid vaporizable material. In one embodiment, the portion of the plurality of particles that are substantially melted are within a predetermined distance of the wicking element.

The liquid vaporizable material can then be drawn into the wicking element, and ultimately vaporized into vaporized material. The liquid vaporizable material can be substantially vaporized by the wicking element itself, either by the same amount of heat provided to substantially cause the solid to liquid phase change or by an additional amount of heat provided by the wicking element. Alternatively, or in addition, the liquid vaporizable material can be substantially vaporized by a separate heating element.

While the cartridges are shown and described in connection with a plurality of particles of vaporizable material, a person skilled in the art will appreciate that these cartridges can be used in connection with vaporizable material in other shapes and sizes. Moreover, the implementation of storing a plurality of particles that are configured for on-demand liquid vaporizable material formation is not limited to the cartridges shown and described herein.

Figure 2:
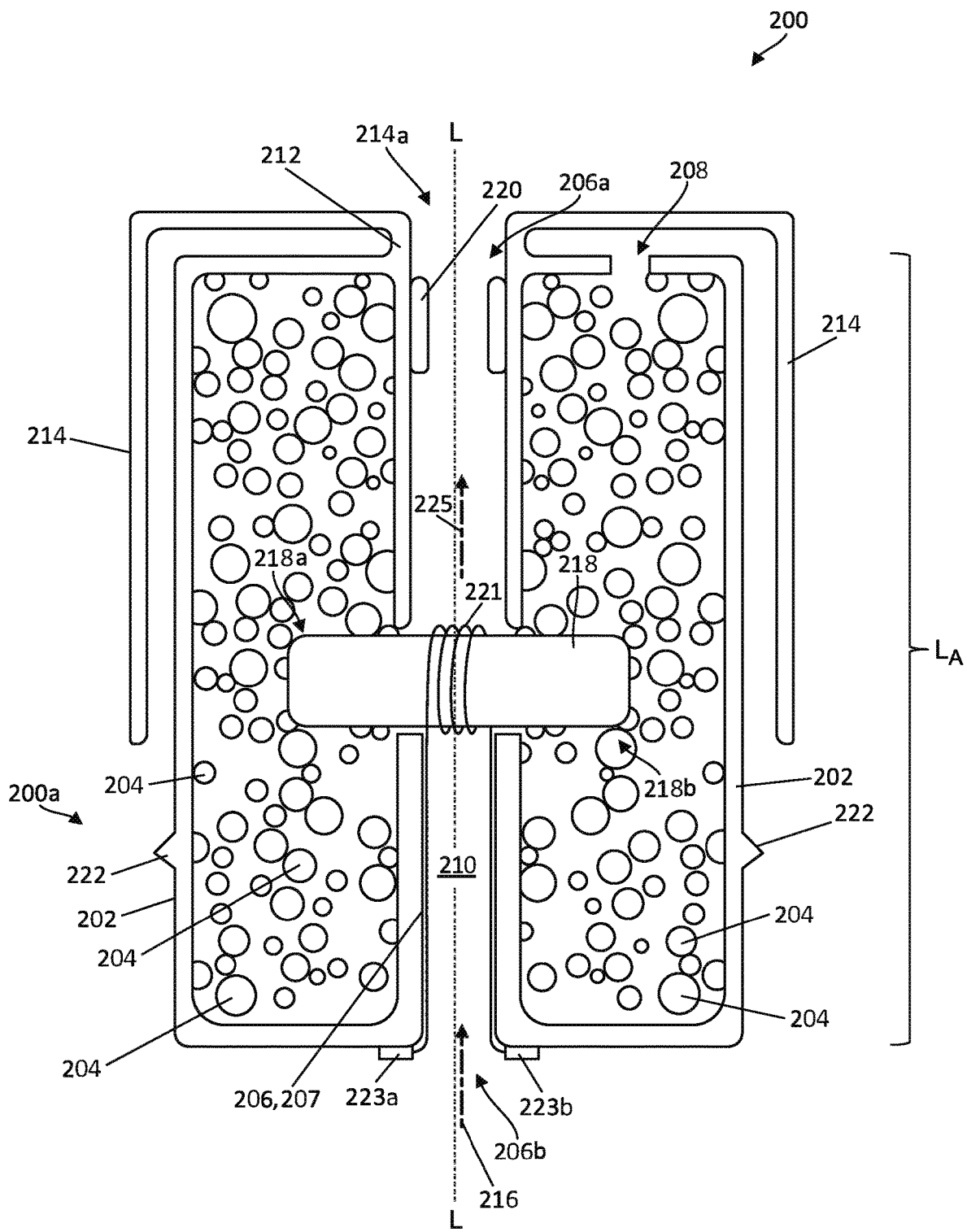
FIG. 2 illustrates a schematic of another embodiment of a vaporizer cartridge.

FIG. 2 illustrates an exemplary vaporizer cartridge 200 that can be selectively coupled to and removable from a vaporizer body, such as vaporizer body 110 shown in FIGS. 1A-1D. More specifically, the cartridge 200 includes a reservoir 202 configured to contain a plurality of encapsulated particles 204 and an airflow tube 206 extending through the reservoir 202. Alternatively, the cartridge 200 can be configured to contain a plurality of particles formed of substantially solid vaporizable material. For purposes of simplicity, certain components of the cartridge 200 are not illustrated.

As discussed above, each encapsulated particle includes a core and a coating material in which the core is formed of a liquid vaporizable material. While the plurality of encapsulated particles are illustrated as being dispersed throughout the reservoir 202, a person skilled in the art will appreciate that the particles may be, for example, packed within the reservoir 202 at any desired porosity and location. Thus, a porosity with interstices between the encapsulated particles can be tailored to a desired value. In some embodiments, such interstices can be filled with air. Further, the encapsulated particles may possess a selective distribution of sizes, for example, the distribution illustrated in FIG. 2.

While the reservoir 202 can have a variety of shapes and sizes, the reservoir 202, as shown in FIG. 2, is substantially rectangular in shape. The reservoir 202 can include at least one vent 208 that is configured to substantially allow the passage of air into the reservoir 202 from the environment to thereby substantially maintain an inner pressure (e.g., an inner pressure that is substantially equal to ambient pressure) of the reservoir 202. As such, the at least one vent 208 can function as a one-way valve and therefore can be used to decrease or eliminate negative pressure that is created within the reservoir 202 (e.g., as liquid vaporizable material flows out of the reservoir 202). The at least one vent 208 can also have a diameter that is less than the diameter(s) of the encapsulated particles so as substantially prevent the encapsulated particles from exiting the reservoir 202 through the at least one vent 208.

While the airflow tube 206 is shown to be approximately centered within respect to a longitudinal axis (L) extending through a centroid of the reservoir 202, such position is not required. As such, other locations of the airflow tube 206 within the reservoir 202 are also contemplated herein. Further, other airflow configurations through the reservoir 202 are also contemplated herein.

The airflow tube 206 can have a variety of configurations. For example, as shown in FIG. 2, the airflow tube extends a length (LA) from a first end 206a to a second end 206b and is defined by a curved sidewall 207. While the airflow tube 206 is illustrated as being open at its first and second ends 206a, 206b, in other embodiments, the airflow tube 26 can also be defined by a bottom wall at the second end 206b of the airflow tube 206. This bottom wall can be configured to substantially allow air to pass therethrough and into the airflow tube 206.

Further, as shown in FIG. 2, the airflow tube 206 defines a passageway 210 that extends therethrough and into communication with an outlet tube 212 of a mouthpiece 214 of the cartridge 200. The outlet tube 212 extends from and is in communication with an outlet 214a of the mouthpiece 214. The passageway 210 is configured to direct air, illustrated as arrow 216, through the airflow tube 206 so that the air 216 will mix with vaporized material to form an aerosol, illustrated as arrow 225, as discussed in more detail below. The passageway 210 further directs the aerosol 225 through the first end 206a (e.g., an outlet) of the airflow tube 206, and thus into a mouthpiece 214 that is coupled to the vaporizer cartridge 200, for inhalation by a user. The mouthpiece can have a variety of configurations and therefore is not limited to what is illustrated in FIG. 2. While a mouthpiece 214 is shown in FIG. 2, a person skilled in the art will appreciate that in other embodiments, the mouthpiece 214 can be omitted and the user can directly puff on the cartridge 200 at an outlet (such as the first end 206a of the airflow tube 206).

As further shown in FIG. 2, the airflow tube 206 includes a wicking element 218. As discussed above, the wicking element 218 is configured to draw a portion of liquid vaporizable material into the airflow tube 206 for vaporization when at least a portion of the plurality of encapsulated particles 204 are ruptured. Further, as discussed above, the wicking element 218 can also be further configured to be selectively bulk heated so as to thermally rupture a portion of the shells of the plurality of encapsulated particles 204 to release the liquid vaporizable material therefrom.

While the wicking element 218 can have a variety of configurations, the wicking element 218 is substantially rectangular. The wicking element 218 extends substantially laterally across the airflow tube 206 (e.g., substantially perpendicular to the length (LA) of the airflow tube 206) such that a first and a second opposing end 218a, 218b of the wicking element 218 are each positioned within the reservoir 202. As such, the wicking element 218 is in fluid communication with the reservoir 202.

In use, once liquid vaporizable material is drawn into the airflow tube 206 via the wicking element 218, as discussed above, it can be substantially vaporized into vaporized material via heating element 221, as discussed in more detail below. The vaporized material mixes with the air 216 passing through the passageway 210 to form the aerosol 225 and is carried out of the airflow tube 206 and into the outlet tube 212 and ultimately through the outlet 214a of the mouthpiece 214 for inhalation by a user.

As further shown in FIG. 2, the vaporizer cartridge 200 includes a heating element 221 disposed within the airflow tube 206. The heating element 221 is configured to vaporize at least a portion of the vaporizable material drawn into the wicking element 218, and thus into the airflow tube 206. The heating element 221 can be or include one or more of a conductive heater, a radiative heater, and a convective heater. As discussed above, one type of heating element is a resistive heating element, such as a resistive coil, which can be constructed of or at least include a material (e.g., a metal or alloy, for example a nickel-chromium alloy, or a non-metallic resistor) configured to dissipate electrical power in the form of heat when electrical current is passed through one or more resistive segments of the heating element. As shown in FIG. 2, the heating element 221 is in the form of a resistive coil.

In some embodiments, the vaporizer cartridge 200 includes two or more cartridge contacts such as, for example, a first cartridge contact 223a and a second cartridge contact 223b. The two or more cartridge contacts can be configured to couple, for example, with the receptacle contacts 125a and 125b in order to form one or more electrical connections with the vaporizer body 110. The circuit completed by these electrical connections can allow delivery of electrical current to the heating element 221. The circuit can also serve additional functions such as, for example, measuring a resistance of the heating element 221 for use in determining and/or controlling a temperature of the heating element 221 based on a thermal coefficient of resistivity of the heating element 221.

The cartridge 200 can also include a spit-catch element 220 that is disposed within the airflow tube 206. The spit-catch element 220 can be configured to prevent the ingress of external material (e.g., saliva and/or the like) into passageway 210 including by capturing the external material. While the spit-catch element can be disposed within any portion of the airflow tube 206, the spit-catch element 220 is disposed proximate to the first end 206a of the airflow tube 206. The spit-catch element 220 can have a variety of configurations. As shown, the spit-catch element 200 is substantially cylindrical and coupled to the curved sidewall 207 of the airflow tube 206. Further, the cartridge 200 can also include an attachment structure 222 for coupling to a vaporizer body, such as vaporizer body 110 (FIGS. 1A-1D). In some embodiments, the attachment structure 222 of the cartridge 200 is a male coupling element, whereas in other embodiments, the attachment structure 222 of the cartridge 200 is a female coupling element. For example, as shown in FIG. 2, the attachment structure 222 is a male coupling element that is in the form of a protrusion that is configured to be received within a female coupling element (e.g., recess) that can fit and/or otherwise snap over such protrusions when an end 200a of the cartridge 200 is inserted into a vaporizer body. Other various configurations of suitable attachment structures are contemplated herein, e.g., structures that are configured for a friction fit. It is also contemplated herein that a spit-catch element and/or an attachment structure can be omitted.

Terminology

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a," "an," and "the" are intended to include the plural forms as well, unless the context clearly indicates otherwise.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Use of the term "based on," herein and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described herein can be directed to various combinations and subcombinations of the disclosed features and/or combinations and subcombinations of several further features disclosed herein. In addition, the logic flows depicted in the accompanying figures and/or described herein do not necessarily require the particular order shown, or sequential order, to achieve desirable results. Other implementations may be within the scope of the following claims.

What is claimed is:

1. A cartridge for a vaporizer device, the cartridge comprising:
    a reservoir configured to contain a plurality of encapsulated particles, each of the plurality of encapsulated particles includes a core formed of a liquid vaporizable material and a coating material that forms a shell surrounding the core, wherein the shells of the plurality of encapsulated particles are configured to be selectively ruptured to release the liquid vaporizable material therefrom; and
    an airflow tube extending through the reservoir, the airflow tube including a wicking element that is in communication with the reservoir, wherein the wicking element is configured to draw, into the airflow tube for vaporization, at least a portion of the liquid vaporizable material that is released by rupturing one or more shells of the plurality of encapsulated particles;
    wherein the wicking element is configured to be selectively bulk heated to thermally rupture a portion of the shells of the plurality of encapsulated particles to release the liquid vaporizable material therefrom.

2. The cartridge of claim 1, wherein the wicking element is configured to substantially draw at least a portion of ruptured shells into the airflow tube for vaporization.

3. The cartridge of claim 2, wherein the vaporization of the portion of the ruptured shells drawn into the airflow tube occurs concurrently with the vaporization of the liquid vaporizable material.

4. The cartridge of claim 1, wherein another portion of the shells of the plurality of encapsulated particles are configured to be mechanically ruptured.

5. The cartridge of claim 1, wherein another portion of the shells of the plurality of encapsulated particles are configured to be chemically ruptured.

6. The cartridge of claim 1, wherein the portion of the shells that are ruptured are within a predetermined distance of the wicking element.

7. The cartridge of claim 1, wherein the wicking element is configured to receive at least a portion of the released liquid vaporizable material under the influence of gravity.

8. The cartridge of claim 1, wherein the reservoir includes at least one vent that is configured to substantially allow air to pass into the reservoir.

9. The cartridge of claim 8, wherein the at least one vent is configured to inhibit the plurality of encapsulated particles to pass therethrough and out of the reservoir.

10. The device of claim 1, wherein the reservoir includes at least one vent that is configured to substantially allow air to pass into the reservoir.

11. The device of claim 10, wherein the at least one vent is configured to inhibit the plurality of encapsulated particles to pass therethrough and out of the reservoir.

12. A cartridge for a vaporizer device, the cartridge comprising:
    a reservoir configured to contain a plurality of particles, each particle of the plurality of particles being formed of a substantially solid vaporizable material; and
    an airflow tube extending through the reservoir, the airflow tube including a wicking element that is in communication with the reservoir, wherein the wicking element is configured to be selectively bulk heated to cause a portion of the plurality of particles to be substantially melted to form a liquid vaporizable material, and wherein the wicking element is configured to draw the liquid vaporizable material into the airflow tube for vaporization.

13. The cartridge of claim 12, wherein the wicking element is configured to receive at least a portion of the liquid vaporizable material under the influence of gravity.

14. The cartridge of claim 12, wherein the reservoir includes at least one vent that is configured to substantially allow air to pass into the reservoir.

15. The cartridge of claim 14, wherein the at least one vent is configured to substantially inhibit the plurality of particles to pass therethrough and out of the reservoir.

16. The cartridge of claim 12, wherein the portion of the plurality of particles that are substantially melted are within a predetermined distance of the wicking element.

17. A vaporizer device, comprising:
    a vaporizer body; and
    a cartridge that is selectively coupled to and removable from the vaporizer body, the cartridge including:

a reservoir configured to contain a plurality of encapsulated particles, each of the plurality of encapsulated particles includes a core formed of a liquid vaporizable material and a coating material that forms a shell surrounding the core, wherein the shells of the plurality of encapsulated particles are configured to be selectively ruptured to release the liquid vaporizable material therefrom, and an airflow tube extending through the reservoir, the airflow tube including a wicking element that is in communication with the reservoir, wherein the wicking element is configured to draw, into the airflow tube for vaporization, at least a portion of the liquid vaporizable material that is released by rupturing one or more shells of the plurality of encapsulated particles;

wherein the wicking element is configured to selectively bulk heated to thermally rupture a portion of the shells of the plurality of encapsulated particles to release the liquid vaporizable material therefrom.

18. The device of claim 17, wherein the wicking element is configured to receive at least a portion of the released liquid vaporizable material under the influence of gravity.

19. The device of claim 17, wherein the cartridge includes a spit-catch element that is disposed within the air-flow tube.

20. The device of claim 17, wherein the cartridge includes an attachment structure for coupling to the vaporizer body.

* * * * *